(12) United States Patent
Düx et al.

(10) Patent No.: US 8,003,817 B2
(45) Date of Patent: Aug. 23, 2011

(54) PROCESS FOR THE PREPARATION OF DIARYL CARBONATES OR ARYLALKYL CARBONATES FROM DIALKYL CARBONATES

(75) Inventors: Andre Düx, Brühl (DE); Pieter Ooms, Krefeld (DE); Johann Rechner, Kempen (DE); Kaspar Hallenberger, Leverkusen (DE); Georg Ronge, Düsseldorf (DE); Johan Vanden Eynde, Zwijnaarde (BE)

(73) Assignee: Bayer MaterialScience AG, Leverkusen (DE)

( * ) Notice: Subject to any disclaimer, the term of this patent is extended or adjusted under 35 U.S.C. 154(b) by 303 days.

(21) Appl. No.: 12/121,873

(22) Filed: May 16, 2008

(65) Prior Publication Data

US 2008/0293960 A1 Nov. 27, 2008

(30) Foreign Application Priority Data

May 25, 2007 (DE) .......................... 10 2007 024 574

(51) Int. Cl.
*C07C 69/96* (2006.01)
(52) U.S. Cl. ........................................ 558/274
(58) Field of Classification Search .................. 558/274
See application file for complete search history.

(56) References Cited

U.S. PATENT DOCUMENTS

| | | | |
|---|---|---|---|
| 3,642,858 A | 2/1972 | Frevel et al. | |
| 3,803,201 A | 4/1974 | Gilpin et al. | |
| 4,181,676 A | 1/1980 | Buysch et al. | |
| 4,252,737 A | 2/1981 | Krimm et al. | |
| 4,330,665 A | 5/1982 | Krimm et al. | |
| 4,552,704 A | 11/1985 | Mark | |
| 4,554,110 A | 11/1985 | Mark | |
| 5,008,046 A | 4/1991 | Bremus et al. | |
| 5,334,742 A | 8/1994 | Schön et al. | |
| 5,344,954 A | 9/1994 | Schön et al. | |
| 5,354,923 A | 10/1994 | Schön et al. | |
| 6,515,187 B1 | 2/2003 | Schon et al. | |
| 7,254,069 B2 | 8/2007 | Haraguchi et al. | |
| 7,288,668 B2 * | 10/2007 | Ryu et al. | 558/274 |
| 7,417,161 B2 * | 8/2008 | Woo et al. | 558/270 |
| 2008/0223711 A1 | 9/2008 | Fukuoka et al. | |

FOREIGN PATENT DOCUMENTS

| | | |
|---|---|---|
| DE | 258412 | 4/1913 |
| DE | 3445552 A1 | 7/1985 |
| DE | 3445555 A1 | 7/1985 |
| DE | 3809417 A1 | 10/1989 |
| DE | 4006420 A1 | 9/1991 |
| DE | 4036594 A1 | 5/1992 |
| DE | 4226755 A1 | 2/1994 |
| DE | 4226756 A1 | 2/1994 |
| EP | 0000879 A1 | 3/1979 |
| EP | 0000880 A1 | 3/1979 |
| EP | 0001082 A1 | 3/1979 |
| EP | 0039452 A2 | 11/1981 |
| EP | 0338760 A2 | 10/1989 |
| EP | 0461274 A1 | 12/1991 |
| EP | 0781760 A1 | 7/1997 |
| GB | 25338 | 3/1912 |
| JP | 54-125617 | 9/1979 |
| JP | 57-176932 | 10/1982 |
| JP | 61172852 | 4/1986 |
| JP | 64-005588 | 1/1989 |
| JP | 01-093580 | 4/1989 |
| JP | 2001093560 | 4/2001 |
| JP | 2004/063023 | 2/2004 |
| WO | WO-2004/016577 A1 | 2/2004 |
| WO | WO-2006/001256 A1 | 1/2006 |
| WO | WO-2006035642 A1 | 4/2006 |

OTHER PUBLICATIONS

Agrawal, R., et al., *On the Use of Intermediate Reboilers in the Rectifying Section and Condensers in the Stripping Section of a Distillation Column*, Ind. Eng. Chem. Res., 1996, Bd. 35, pp. 2801-2807.

European Search and Preliminary Examination Report in European Application 08008796.8 mailed May 7, 2010.

* cited by examiner

*Primary Examiner* — Rei-tsang Shiao
(74) *Attorney, Agent, or Firm* — Connolly Bove Lodge & Hutz LLP

(57) ABSTRACT

The invention provides a process for the preparation of diaryl carbonates and/or alkylaryl carbonates from dialkyl carbonates and aromatic hydroxy compounds using one or more intermediate condensers for improving heat integration.

14 Claims, 3 Drawing Sheets

Figure 1:
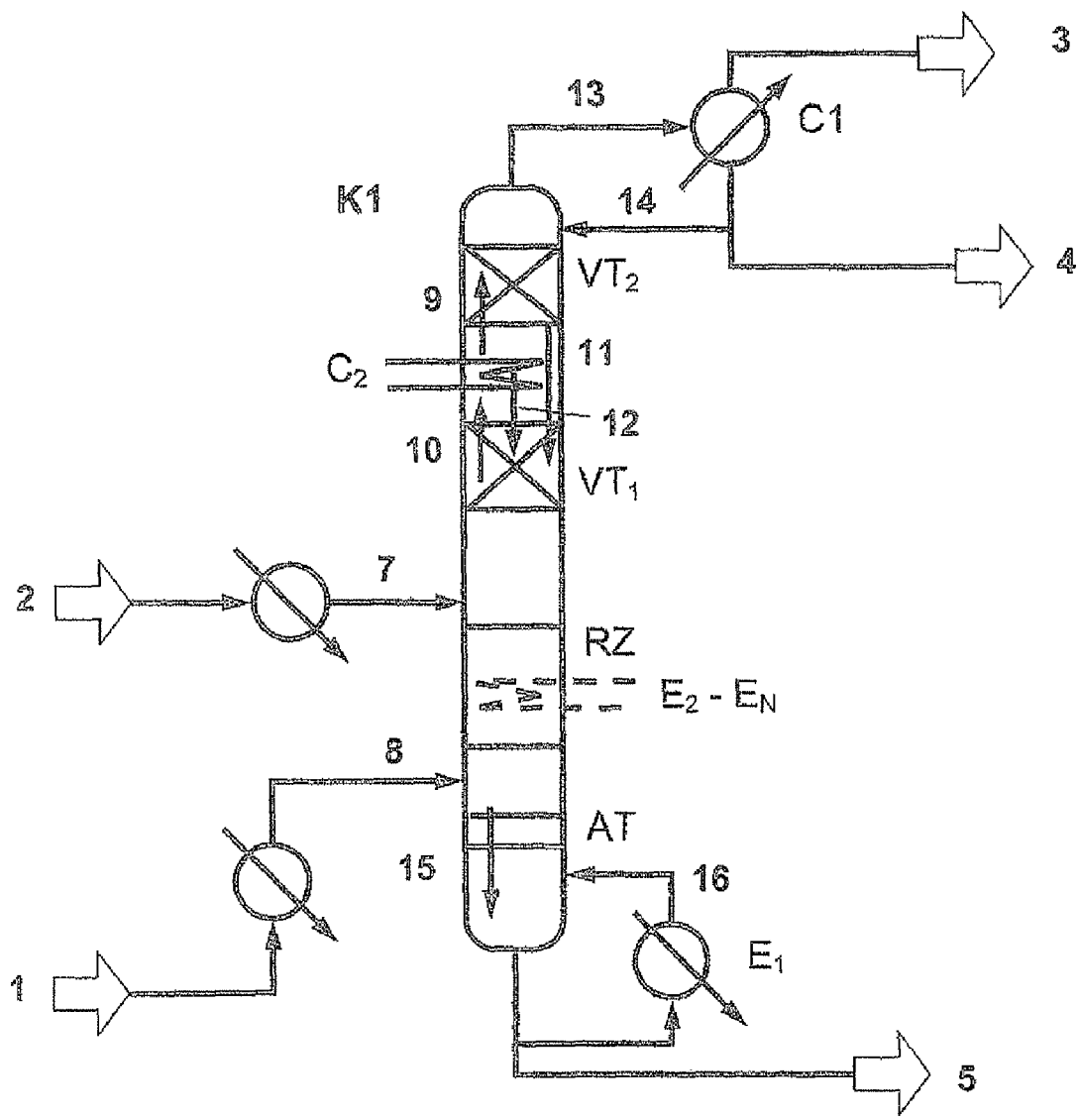

PROCESS FOR THE PREPARATION OF DIARYL CARBONATES OR ARYLALKYL CARBONATES FROM DIALKYL CARBONATES

RELATED APPLICATIONS

This application claims benefit to German Patent Application No. 10 2007 024574 filed May 25, 2007. German Patent Application No. 10 2007 024574 and the references cited therein are incorporated by reference in its entirety for all useful purposes.

FIELD OF INVENTION

The invention provides a process for the preparation of diaryl carbonates and/or alkylaryl carbonates from dialkyl carbonates and aromatic hydroxy compounds using at least one reaction column having one or more intermediate condensers for improving heat integration.

BACKGROUND OF THE INVENTION

The preparation of aromatic and aliphatic-aromatic carbonic acid esters (carbonates) by transesterification starting from aliphatic carbonic acid esters and aromatic hydroxy compounds is known in principle. It is an equilibrium reaction in which the position of equilibrium is shifted almost completely towards the aliphatically substituted carbonates. It is therefore comparatively simple to prepare aliphatic carbonates from aromatic carbonates and alcohols. However, in order to carry out the reaction in the opposite direction, in the direction towards aromatic carbonates, it is necessary effectively to shift the equilibrium, which is positioned very unfavourably, to the side of the aromatic carbonates, it being necessary to use not only very active catalysts but also suitable procedures.

It is known to carry out such equilibrium reactions in columns and thus advantageously shift them towards the formation of the desired product (e.g. U. Block, Chem.-Ing. Techn. 49, 151 (1977); DE-OS 38 09 417; B. Schleper, B. Gutsche, J. Wnuck and L. Jeromin, Chem.-Ing.-Techn. 62, 226 (1990); Ullmanns Encyclopädie der techn. Chemie, 4th Edition, Vol. 3; p. 375 ff. 1973).

In the known processes, the transesterification is therefore also preferably carried out continuously as a countercurrent transesterification in one or more reaction columns.

EP-A 0 461 274 describes a continuous transesterification process for the preparation of aromatic carbonates in one or in a plurality of multistage columns connected in series, wherein dialkyl carbonates or alkylaryl carbonates are reacted with phenols and the readily volatile products, namely the reaction alcohols and dialkyl carbonates, are removed at the head of the columns and the high-boiling products, such as, for example, diaryl carbonates, are removed at the sump of the columns. Particular process measures which allow the transesterification to be carried out more advantageously by adapting the apparatus and procedures to the above-described special problems of this transesterification are not described, however. In particular, there is no indication for the person skilled in the art whether the column used for the transesterification is preferably constructed with or without a concentrating part.

In a construction with a concentrating part, the vaporous mixture removed at the head of the column contains substantially the dialkyl carbonate used in excess in the reaction and the corresponding alcohol formed in the reaction, and the condensation of the mixture takes place at a temperature below the evaporation temperature of the dialkyl carbonate at the pressure prevailing in the reaction, with the result that the heat of condensation that is obtained can be dissipated only at a low temperature level compared with the temperature in the reaction zone. If the transesterification column is constructed without a concentrating part, then the vapour mixture removed at the head of the column, and accordingly also the distillate from the column, contains not inconsiderable amounts of the aromatic hydroxy compounds used for the reaction and, optionally, also of even higher-boiling components.

When the dialkyl carbonate used in excess is recovered, for example by separation from the reaction alcohol by distillation, amounts of higher-boiling components, such as, for example, the aromatic hydroxy compound, lead to an additional separation problem or at least to an increased temperature level during the supply of heat.

DE-A 42 26 756 describes a two-stage process for the preparation of diaryl carbonates, in which in a first stage an aromatic hydroxy compound is reacted with a dialkyl carbonate in a countercurrent transesterification, there being used a countercurrent transesterification column which can be constructed both with and without a concentrating part. In the case of an arrangement with a concentrating part, the temperature level in the condensation is comparatively low, so that the heat of condensation formed thereby cannot be used economically for operating other process sections. In the case of an arrangement without a concentrating part, the distillate, as well as containing the dialkyl carbonate and the alcohol formed in the reaction, additionally also contains a high proportion of the aromatic hydroxy compound. During recovery of the dialkyl carbonate, this leads to an increased temperature level in the region of the column sump, which makes the supply of energy at that point more difficult.

DE-A 42 26 755 describes a process for the preparation of diaryl carbonates in two reaction columns which are coupled with one another in terms of energy and materials, wherein an aromatic hydroxy compound and a dialkyl carbonate are reacted in the first stage, and the alkylaryl carbonate formed thereby is converted into the diaryl carbonate in the second stage either by transesterification with the aromatic hydroxy compound or by disproportionation. However, a problem with this process is that, owing to the integration of the process in terms of energy and materials, the reaction conditions for the formation of the alkylaryl or diaryl carbonate cannot be chosen optimally because they are determined by the almost identical pressure prevailing in the two steps. Accordingly, the described process does not bring any advantages in terms of energy integration.

EP-A 781 760 describes a continuous process for the preparation of aromatic carbonates by reacting a dialkyl carbonate with an aromatic hydroxy compound in the presence of a catalyst and continuously removing the aromatic carbonate formed in the reaction, the alcoholic secondary products, the dialkyl carbonate and the aromatic hydroxy compound, the dialkyl carbonate and the aromatic hydroxy compound being fed back into the reaction again. Although the described process steps are effective as regards the reaction procedure in terms of a high space-time yield and as regards working-up in terms of an as efficient separating sequence as possible, the process does not exhibit any possibilities for integration of the reaction and the working-up steps in terms of energy.

WO-A 2006/001256 describes a process in which an aromatic hydroxy compound is reacted with a dialkyl carbonate in the presence of a catalyst, as well as a technical device suitable therefor. Here too, no reference points are given for energy integration.

Without appropriately efficient energy integration, the energy consumption of the processes described hereinbefore is known to be high, which in turn raises questions about the advantageousness of the phosgene-free preparation of aryl carbonates from an ecological and economic point of view.

WO-A 2004/016577 describes a process for the preparation of aromatic carbonates from dialkyl carbonate and an aromatic hydroxy compound in the presence of a catalyst in a plurality of separate, series-connected reaction zones of a reactor arrangement, wherein the heat of condensation that is formed in the condensation of the vapour stream of the last reaction zone is used to heat the liquid stream introduced into the first reaction zone. However, this process has the disadvantage that the reactor arrangement is complex. In addition, the energy integration of this process is worthy of improvement.

SUMMARY OF THE INVENTION

Accordingly, there was a continued need to provide a process for the preparation of aromatic carbonates, i.e. diaryl and/or alkylaryl carbonates, preferably diaryl carbonates, which does not exhibit the above-mentioned disadvantages and in which, as compared with the known processes mentioned hereinbefore, energy integration is possible in an efficient manner, or improved energy integration can be achieved.

Accordingly, the object underlying the invention was to provide a process for the preparation of aromatic carbonates, i.e. diaryl and/or alkylaryl carbonates, preferably diaryl carbonates, in which, as compared with known processes, energy integration is possible in an efficient manner, or improved energy integration can be achieved.

This object is achieved according to the invention in that, by the suitable use of one or more intermediate condensers in a process for the preparation of aromatic carbonates, i.e. diaryl and/or alkylaryl carbonates, from dialkyl carbonates and aromatic hydroxy compounds, the energy integration can be markedly improved while the procedure is simple.

The present invention therefore provides a process for the preparation of at least one diaryl carbonate and/or alkylaryl carbonate from at least one dialkyl carbonate and at least one aromatic hydroxy compound which comprises
(a) reacting the at least one dialkyl carbonate(s) in the presence of at least one transesterification catalyst with the aromatic hydroxy compound(s) in at least one transesterification column containing at least one concentrating part in the upper portion of the column and at least one reaction zone beneath the concentrating part, which has at least two sections,
(b) removing the vapor at the head of the transesterification column is condensed wholly or partially in at least one condenser,
equipping at least one concentrating part of the transesterification column with at least one intermediate condenser, and the heat of condensation obtained by condensation in that intermediate condenser is fed directly or indirectly back into the process again.

A BRIEF DESCRIPTION OF THE FIGURES

FIG. 1 describes a reactive rectification in the transesterification column having an intermediate condenser in general.

Figure 2:
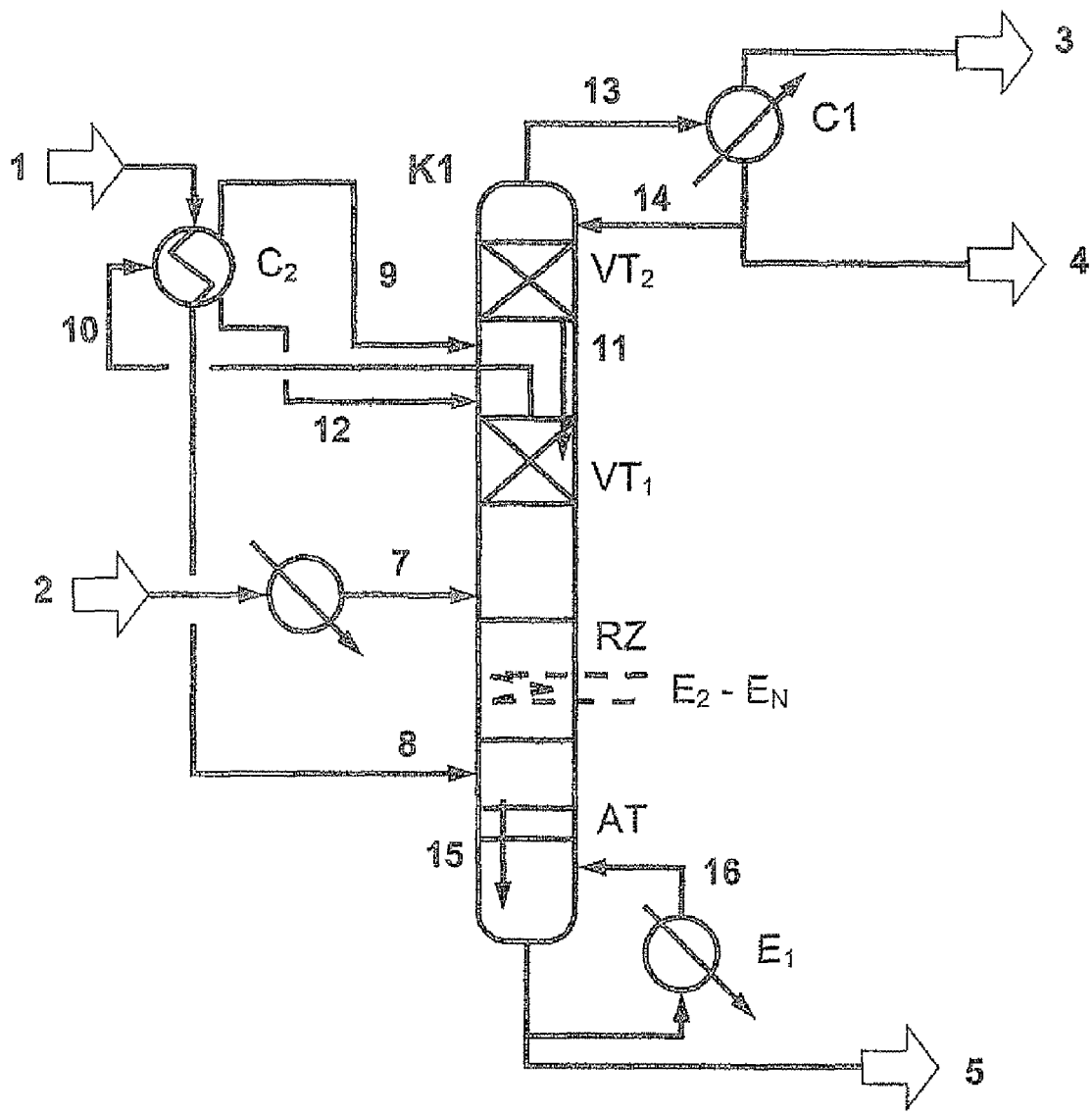

FIG. 2 describes a reactive rectification with an external arrangement of the intermediate condenser and combination with the evaporation of the dialkyl carbonate for feeding back the resulting heat of condensation.

Figure 3:
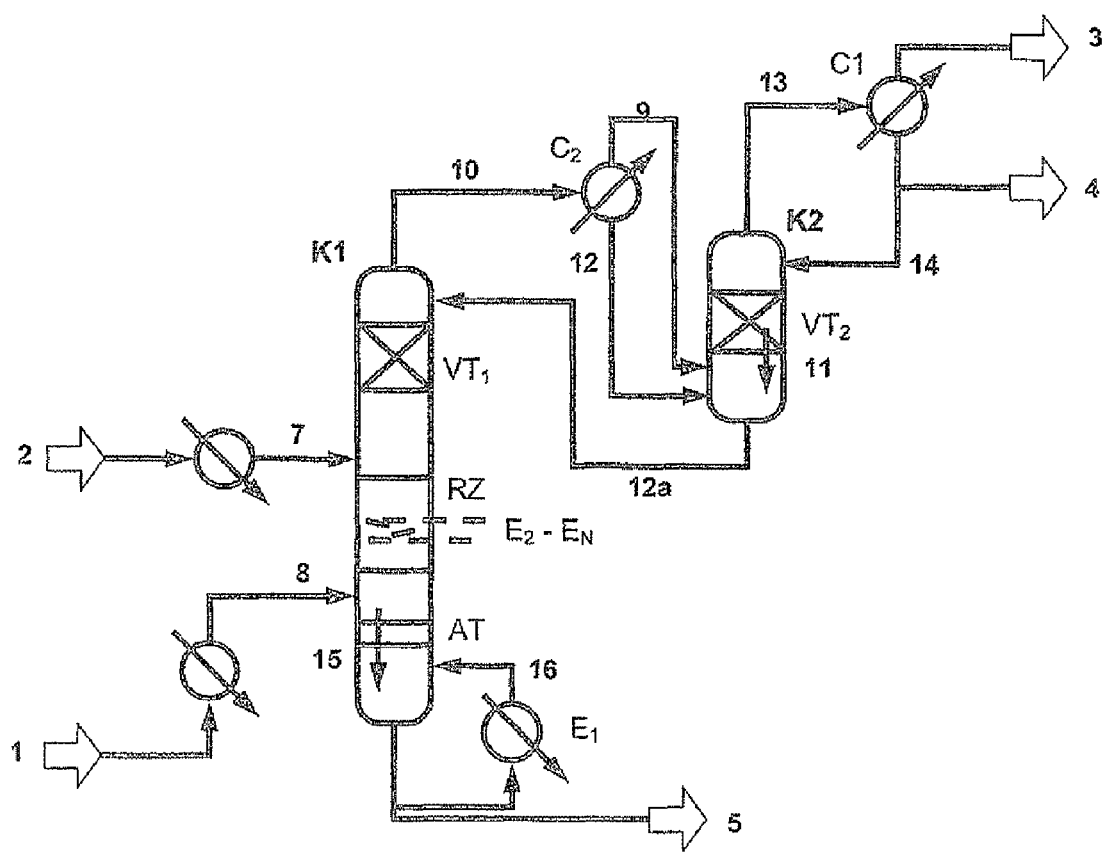

FIG. 3 describes a reactive rectification with an external arrangement of the intermediate condenser and an external arrangement of the upper concentrating part in a separate column.

DETAILED DESCRIPTION OF THE INVENTION

As used herein, the singular terms "a" and "the" are synonymous and used interchangeably with "one or more." Accordingly, for example, reference to "a column" herein or in the appended claims can refer to a single column or more than one column. Additionally, all numerical values, unless otherwise specifically noted, are understood to be modified by the word "about."

Diaryl carbonates prepared within the scope of the invention are preferably those of the general formula (I)

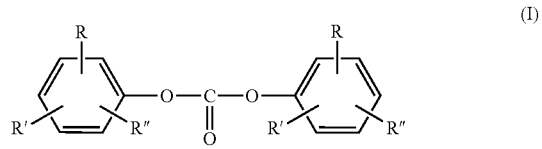

(I)

wherein R, R' and R" independently of one another represent H, linear or branched, optionally substituted $C_1$-$C_{34}$-alkyl, preferably $C_1$-$C_6$-alkyl, particularly preferably $C_1$-$C_4$-alkyl, $C_1$-$C_{34}$-alkoxy, preferably $C_1$-$C_6$-alkoxy, particularly preferably $C_1$-$C_4$-alkoxy, $C_5$-$C_{34}$-cycloalkyl, $C_7$-$C_{34}$-alkylaryl, $C_6$-$C_{34}$-aryl or a halogen radical, preferably a chlorine radical, and R, R' and R" on both sides of formula (I) can be the same or different. R can also represent —COO—R'", wherein R'" can be H, optionally branched $C_1$-$C_{34}$-alkyl, preferably $C_1$-$C_6$-alkyl, particularly preferably $C_1$-$C_4$-alkyl, $C_1$-$C_{34}$-alkoxy, preferably $C_1$-$C_{16}$-alkoxy, particularly preferably $C_1$-$C_4$-alkoxy, $C_5$-$C_{34}$-cycloalkyl, $C_7$-$C_{34}$-alkylaryl or $C_6$-$C_{34}$-aryl. Preferably, R, R' and R" on both sides of formula (I) are the same. Most particularly preferably, R, R' and R" represent H.

Diaryl carbonates of the general formula (I) are, for example: diphenyl carbonate, methylphenyl-phenyl carbonates and di-(methylphenyl) carbonates, also in the form of a mixture, wherein the methyl group can be in any desired position on the phenyl rings, as well as dimethylphenyl-phenyl carbonates and di-(dimethylphenyl) carbonates, also in the form of a mixture, wherein the methyl groups can be in any desired position on the phenyl rings, chlorophenyl-phenyl carbonates and di-(chlorophenyl) carbonates, wherein the methyl group can be in any desired position on the phenyl rings, 4-ethylphenyl-phenyl carbonate, di-(4-ethylphenyl) carbonate, 4-n-propylphenyl-phenyl carbonate, di-(4-n-propylphenyl) carbonate, 4-isopropylphenyl-phenyl carbonate, di-(4-isopropylphenyl) carbonate, 4-n-butylphenyl-phenyl carbonate, di-(4-n-butylphenyl) carbonate, 4-isobutylphenyl-phenyl carbonate, di-(4-isobutylphenyl) carbonate, 4-tert-butylphenyl-phenyl carbonate, di-(4-tert-butylphenyl) carbonate, 4-n-pentylphenyl-phenyl carbonate, di-(4-n-pentylphenyl) carbonate, 4-n-hexylphenyl-phenyl carbonate, di-(4-n-hexylphenyl) carbonate, 4-isooctylphenyl-phenyl carbonate, di-(4-isooctylphenyl) carbonate, 4-n-nonylphenyl-phenyl carbonate, di-(4-n-nonyl-phenyl) carbonate, 4-cyclohexylphenyl-phenyl carbonate, di-(4-cyclohexylphenyl) carbonate, 4-(1-methyl-1-phenylethyl)-phenyl-phenyl carbonate, di-[4-(1-methyl-1-phenylethyl)-phenyl]carbonate, biphenyl-4-yl-phenyl carbonate, di-(biphenyl-4-yl) carbonate, (1-naphthyl)-phenyl carbonate, (2-naphthyl)-phenyl carbonate, di-(1-naphthyl) carbonate, di-(2-naphthyl) carbonate, 4-(1-naphthyl)-phenyl-phenyl carbonate, 4-(2-naphthyl)-phenyl-phenyl carbonate, di-[4-(1-naphthyl)-phenyl] carbonate, di-[4-(2-naphthyl)phenyl]carbonate, 4-phenoxyphenyl-phenyl carbonate, di-(4-phenoxyphenyl) carbonate, 3-pentadecylphenyl-phenyl carbonate, di-(3-pentadecylphenyl) carbonate, 4-tritylphenyl-phenyl carbonate, di-(4-tritylphenyl) carbonate, methyl salicylate-phenyl carbonate, di-(methyl salicylate) carbonate, ethyl salicylate-phenyl carbonate, di-(ethyl salicylate) carbonate, n-propyl salicylate-phenyl carbonate, di-(n-propyl salicylate) carbonate, isopropyl salicylate-phenyl carbonate, di-(isopropyl salicylate) carbonate, n-butyl salicylate-phenyl carbonate, di-(n-butyl salicylate) carbonate, isobutyl salicylate-phenyl carbonate, di-(isobutyl salicylate) carbonate, tert-butyl salicylate-phenyl carbonate, di-(tert-butyl salicylate) carbonate, di-(phenyl salicylate)-carbonate and di-(benzyl salicylate) carbonate.

Preferred diaryl carbonates are: diphenyl carbonate, 4-tert-butylphenyl-phenyl carbonate, di-(4-tert-butylphenyl) carbonate, biphenyl-4-yl-phenyl carbonate, di-(biphenyl-4-yl) carbonate, 4-(1-methyl-1-phenylethyl)-phenyl-phenyl carbonate and di-[4-(1-methyl-1-phenylethyl)-phenyl]carbonate.

Diphenyl carbonate is particularly preferred.

Dialkyl carbonates which are preferably used within the scope of the invention are those of formula (II)

wherein $R^1$ and $R^2$ independently of one another represent linear or branched, optionally substituted $C_1$-$C_{34}$-alkyl, preferably $C_1$-$C_6$-alkyl, particularly preferably $C_1$-$C_4$-alkyl. $R^1$ and $R^2$ can be the same or different. $R^1$ and $R^2$ are preferably the same.

$C_1$-$C_4$-Alkyl within the scope of the invention represents, for example, methyl, ethyl, n-propyl, isopropyl, n-butyl, sec-butyl, tert-butyl, $C_1$-$C_6$-alkyl additionally represents, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl, $C_1$-$C_{34}$-alkyl additionally represents, for example, n-heptyl and n-octyl, pinacyl, adamantyl, the isomeric menthyls, n-nonyl, n-decyl, n-dodecyl, n-tridecyl, n-tetradecyl, n-hexadecyl or n-octadecyl. The same applies for the corresponding alkyl radical in, for example, aralkyl or alkylaryl radicals. Alkylene radicals in the corresponding hydroxyalkyl or aralkyl or alkylaryl radicals represent, for example, the alkylene radicals corresponding to the above alkyl radicals.

Aryl represents a carbocyclic aromatic radical having from 6 to 34 skeletal carbon atoms. The same applies for the aromatic part of an arylalkyl radical, also referred to as an aralkyl radical, as well as for aryl constituents of more complex groups, such as, for example, arylcarbonyl radicals.

Arylalkyl and aralkyl, each independently of the other, denote a straight-chained, cyclic, branched or unbranched alkyl radical according to the above definition which can be monosubstituted, polysubstituted or completely substituted by aryl radicals according to the above definition.

The above lists are given by way of example, without implying any limitation.

Preferred dialkyl carbonates are dimethyl carbonate, diethyl carbonate, di(n-propyl) carbonate, di(isopropyl) carbonate, di(n-butyl) carbonate, di(sec-butyl) carbonate, di(tert-butyl) carbonate or dihexyl carbonate. Dimethyl carbonate and diethyl carbonate are particularly preferred. Dimethyl carbonate is most particularly preferred.

Aromatic hydroxy compounds that are suitable within the scope of the invention are preferably those of the general formula (III)

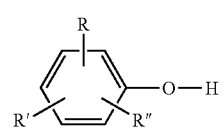

wherein R, R' and R" independently of one another can have the meaning given for the general formula (I).

Such aromatic hydroxy compounds are, for example: phenol, o-, m- or p-cresol, also in the form of a mixture of the cresols, dimethylphenol, also in the form of a mixture, wherein the methyl groups can be in any desired position on the phenol ring, e.g. 2,4-, 2,6- or 3,4-dimethylphenol, o-, m- or p-chlorophenol, o-, m- or p-ethylphenol, o-, m- or p-n-propylphenol, 4-isopropylphenol, 4-n-butylphenol, 4-isobutylphenol, 4-tert-butylphenol, 4-n-pentylphenol, 4-n-hexylphenol, 4-isooctylphenol, 4-n-nonylphenol, o-, m- or p-methoxyphenol, 4-cyclohexylphenol, 4-(1-methyl-1-phenylethyl)-phenol, biphenyl-4-ol, 1-naphthol, 2-1-naphthol, 4-(1-naphthyl)phenol, 4-(2-naphthyl)phenol, 4-phenoxyphenol, 3-pentadecylphenol, 4-tritylphenol, methylsalicylic acid, ethylsalicylic acid, n-propylsalicyclic acid, isopropylsalicylic acid, n-butylsalicylic acid, isobutylsalicylic acid, tert-butylsalicylic acid, phenylsalicylic acid and benzylsalicylic acid.

Preferred diaryl compounds are phenol, 4-tert-butylphenol, biphenyl-4-ol and 4-(1-methyl-1-phenylethyl)-phenol.

Phenol is particularly preferred.

Alkylaryl carbonates prepared within the scope of the invention are preferably those of the general formula (IV)

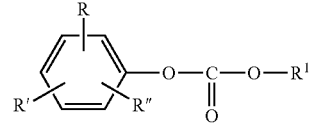

wherein R, R' and R" can have the meaning given for the general formula (I) and $R^1$ can have the meaning given for the general formula (II).

Preferred alkylaryl carbonates are methyl-phenyl carbonate, ethyl-phenyl carbonate, propyl-phenyl carbonate, butylphenyl carbonate and hexyl-phenyl carbonate, methyl-(o-cresyl) carbonate, methyl-(p-cresyl) carbonate, ethyl-(o-cresyl) carbonate, ethyl-(p-cresyl) carbonate, methyl- or ethyl-(p-chlorophenyl) carbonate. Particularly preferred alkylaryl carbonates are methyl-phenyl carbonate and ethyl-phenyl carbonate. Methyl-phenyl carbonate is most particularly preferred.

Both the dialkyl carbonates suitable for the process according to the invention and the aromatic hydroxy compounds are known to the person skilled in the art and are commercially available, or can be prepared by processes which are likewise known to the person skilled in the art.

In the process according to the invention, the aromatic hydroxy compound(s) and the dialkyl carbonate(s) are used in a molar ratio of preferably from 1:0.1 to 1:10, particularly preferably from 1:0.2 to 1:5, most particularly preferably from 1:0.5 to 1:3. The indicated molar ratio does not take into account the feeding of aromatic hydroxy compound or dialkyl carbonate back into the transesterification column via one or more head condenser(s) (see under (b)) or one or more sump evaporator(s) which may be present.

The process according to the invention is carried out in a transesterification column. In preferred embodiments of the process according to the invention, the liquid stream removed at the sump of the transesterification column—optionally after concentration—can be subjected in one or more further steps to a disproportionation, a further transesterification and/or purification. Individual or all such further steps can preferably take place in one or more further columns.

Columns known to the person skilled in the art are suitable as the transesterification column or as optional second or further column(s). These are, for example, distillation or rectification columns, preferably reactive distillation or reactive rectification columns.

The transesterification column contains at least one concentrating part in the upper portion of the column and at least one reaction zone beneath the concentrating part, which has at least two sections, wherein at least one concentrating part of the transesterification column is equipped with at least one intermediate condenser. Each of the two sections, independently of the other, has preferably from 0 to 20, more preferably from 0.1 to 20, theoretical stages. The intermediate condenser is preferably arranged between the two sections of the concentrating part. In that case, the concentrating part is divided into an upper and a lower concentrating part.

The transesterification column is preferably operated countercurrently, the aromatic hydroxy compound preferably being guided in liquid form in at least one reaction zone of the column from the head to the sump and the dialkyl carbonate in gaseous form being guided countercurrently to the liquid stream. The transesterification column is preferably operated in such a manner that there are metered into at least one reaction zone, preferably into the top third of the reaction zone, preferably at the temperature prevailing at that point of the column, one or more streams containing the aromatic hydroxy compound and optionally dissolved transesterification catalyst, in liquid form or with only a low gas content, the gas content preferably being less than 20 wt. %. In addition, one or more streams containing the dialkyl carbonate are passed into the reaction zone, preferably in the bottom third of the reaction zone, the metered addition preferably taking place in gaseous or superheated form. In preferred embodiments, superheating of the vapour stream can be from 0 to 50° C. Furthermore, the temperature of dewpoint is preferably governed by the pressure prevailing in the reaction zone at the point of addition of the particular stream containing dialkyl carbonate.

After passing through the reaction zone(s), the reaction alcohol, after passing through the concentrating part or parts, is removed at the head of the transesterification column. Within the scope of the invention, the reaction alcohol is the alcohol liberated in the transesterification, preferably $R^1$—OH or $R^2$—OH, where $R^1$ and $R^2$ have the meaning given for the general formula (II). In addition to the reaction alcohol, the stream removed at the head of the transesterification column generally also contains excess or unreacted dialkyl carbonate. Owing to the concentrating part(s) present, this stream contains only small amounts of higher-boiling components, such as, for example, the aromatic hydroxy compound. The concentrating part serves to separate the higher-boiling components which are also evaporated in the reaction zone, such as, for example, the aromatic hydroxy compound or alkylaryl carbonate, from the low-boiling reaction alcohols or dialkyl carbonates. This has the advantage that the separation of the reaction alcohols from the dialkyl carbonates can be carried out at a low temperature level.

In preferred embodiments, the transesterification column is operated under reflux conditions. Reflux conditions are to be understood as meaning a procedure in which the vapour stream is condensed partially or completely at the top end of the concentrating part (see under reaction step (b)) and some or all of the condensate formed thereby is fed back at the top end of the concentrating part again as reflux. The reflux ratio is preferably from 0.1 to 20, particularly preferably from 0.1 to 10 and most particularly preferably from 0.1 to 3, the reflux ratio within the scope of the invention corresponding to the weight ratio of condensate fed back into the column to vapour removed at the head of the column without returned condensate.

In preferred embodiments, the transesterification column has at least one stripping part beneath a reaction zone.

The transesterification column can preferably further be equipped with one or more sump evaporator(s). When the transesterification column is constructed with a stripping part, a sump evaporator is preferably also used, the sump evaporator wholly or partially evaporating the liquid flowing from the stripping part. All or part of this wholly or partially evaporated liquid stream is fed back into the transesterification column again. In the case of an embodiment without a stripping part, the liquid flowing from the reaction zone is evaporated wholly or partially in a sump evaporator which is optionally used, and all or part thereof is fed back into the transesterification column again.

The concentrating part of the transesterification column, which is equipped with at least one intermediate condenser, is preferably divided into a lower and an upper concentrating part (two sections), of which the lower concentrating part is located beneath the intermediate condenser and the upper concentrating part is located above the intermediate condenser.

In preferred embodiments, the concentrating part(s) having at least one intermediate condenser can be accommodated in the transesterification column together with the reaction part(s) and optionally at least one stripping part. The vaporous mixture leaving the reaction zone(s) is thereby guided from below into a lower section of the concentrating part, or optionally the lower concentrating part, wherein depletion of the aromatic hydroxy compound takes place. The vaporous mixture leaving this lower section, or optionally the lower concentrating part, is guided into an intermediate condenser, where it partially condenses, and the resulting condensate is supplied at the top end of the lower section of the concentrating part, or optionally the lower concentrating part.

In a further preferred embodiment of the process according to the invention, the intermediate condenser is not integrated in the transesterification column but is in the form of a separate intermediate condenser outside the transesterification column.

In a further preferred embodiment of the process according to the invention, the intermediate condenser and the upper section of the concentrating part are not integrated into the transesterification column but are accommodated separately outside the transesterification column.

Beneath the reaction zone and a stripping part that is optionally present, a mixture containing alkylaryl carbonate, excess or unreacted phenol, diaryl carbonate, transesterification catalysts, dialkyl carbonate, reaction alcohol, and high-boiling compounds formed in the reaction or already present in the starting materials is obtained. When a stripping part is used, the content of low-boiling compounds, such as, for example, dialkyl carbonate and reaction alcohol, is reduced, further alkylaryl carbonate and/or diaryl carbonate being formed under some circumstances in the presence of the transesterification catalyst. The energy required therefor is preferably supplied by one or more evaporators.

In all sections of the transesterification column, that is to say in the concentrating part and optionally the stripping part as well as in the reaction zone, it is possible to use filling materials or regular packing. The filling materials or regular packing to be used are those which are conventional for distillations, as are described, for example, in Ullmann's Encyclopädie der Technischen Chemie, 4th Edition, Vol. 2, p. 528 ff. Examples of filling materials which may be mentioned include Raschig or Pall and Novalox rings, Bert, Intalex or torus saddles, Interpack bodies, and examples of regular packing which may be mentioned include sheet metal and woven packing (such as e.g. BX packing, Montz Pak, Mellapak, Melladur, Kerapak and CY packing) of various materials, such as glass, stoneware, porcelain, stainless steel, plastics material. Preference is given to filling materials and regular packing which have a large surface area and exhibit good wetting as well as an adequate residence time of the liquid phase. These are, for example, Pall and Novolax rings, Berl saddles, BX packing, Montz Pak, Mellapak, Melladur, Kerapak and CY packing.

Alternatively, column plates, such as, for example, perforated plates, bubble-cap plates, valve-type plates and tunnel-type plates, are also suitable. In the reaction zone(s) of the transesterification column, column plates having high residence times with good material exchange, for example bubble-cap plates, valve-type plates or tunnel-type plates having high overflow defences, are particularly preferred. The theoretical plate number of the reaction zone is preferably from 3 to 50, particularly preferably from 10 to 50 and most particularly preferably from 10 to 40. The liquid hold-up is preferably from 1 to 80%, particularly preferably from 5 to 70% and most particularly preferably from 7 to 60% of the inside volume of the column of the reaction zone. The more precise design of the reaction zone(s), of the stripping part that is optionally to be used and of the concentrating part(s) can be carried out by the person skilled in the art.

The temperature of the reaction zone(s) is preferably in the range from 100 to 300° C., particularly preferably from 120 to 250° C., most particularly preferably from 150 to 240° C. In preferred embodiments, an optimal reaction temperature is established in the reaction zone on the one hand by the choice of operating conditions and on the other hand by the additional supply of heat in the region of one or more reaction plates. The supply of heat at the reaction plates can take place either by means of heat exchangers or via reaction plates with the possibility of heat introduction. It is advantageous to carry out the transesterification according to the invention not only at normal pressure but also at elevated or reduced pressure. The pressure of the reaction zone is therefore preferably in the range from 0.5 to 20 bar, particularly preferably from 0.8 to 15 bar, most particularly preferably from 0.9 to 10 bar. The pressures indicated hereinbefore and hereinbelow are absolute pressures, unless explicitly mentioned otherwise.

Transesterification catalysts known from the literature can be used for the reaction steps occurring in the transesterification column. These are transesterification catalysts known from the literature for dialkyl carbonate-phenol transesterification, such as, for example, hydrides, oxides, hydroxides, alcoholates, amides and other salts of alkali and alkaline earth metals, such as of lithium, sodium, potassium, rubidium, caesium, magnesium and calcium, preferably lithium, sodium, potassium, magnesium and calcium, and particularly preferably lithium, sodium and potassium (see e.g. U.S. Pat. Nos. 3,642,858, 3,803,201 or EP-A 1082). Salts of the alkali and alkaline earth metals can also be salts of organic or inorganic acids, such as of acetic acid, propionic acid, butyric acid, benzoic acid, stearic acid, carbonic acid (carbonates or hydrogen carbonates), phosphoric acid, hydrocyanic acid, thiocyanic acid, boric acid, cinnamic acid, $C_{14}$-stannonic acids or antimonic acid. Suitable compounds of the alkali and alkaline earth metals are preferably the oxides, hydroxides, alcoholates, acetates, propionates, benzoates, carbonates and hydrogen carbonates, with particular preference being given to the use of hydroxides, alcoholates, acetates, benzoates or carbonates. The mentioned alkali or alkaline earth metal compounds are preferably used in amounts of from 0.001 to 2 wt. %, more preferably from 0.005 to 0.9 wt. % and particularly preferably from 0.01 to 0.5 wt. %, based on the weight of the reaction mixture to be reacted.

Further catalysts which can be used according to the invention are metal compounds such as $AlX_3$, $TiX_3$, $UX_4$, $TiX_4$, $VOX_3$, $VX_5$, $ZnX_2$, $FeX_3$, $PbX_2$ and $SnX_4$, wherein X represents halogen, acetoxy, alkoxy or aryloxy radicals (DE-OS 2 58 412). Particularly preferred catalysts which can be used according to the invention are metal compounds such as $AlX_3$, $TiX_4$, $PbX_2$ and $SnX_4$, such as, for example, titanium tetrachloride, titanium tetramethoxide, titanium tetraphenoxide, titanium tetraethoxide, titanium tetraisopropylate, titanium tetradodecylate, tin tetraisooctylate and aluminium triisopropylate. Metal compounds $TiX_4$ are most particularly preferred. The mentioned metal compounds are preferably used in amounts of from 0.001 to 5 wt. %, more preferably from 0.005 to 5 wt. % and most particularly preferably from 0.01 to 5 wt. %, based on the weight of the reaction mixture to be reacted.

Within the scope of the invention, halogen denotes fluorine, chlorine or bromine, preferably fluorine or chlorine, particularly preferably chlorine.

Further catalysts which can be used according to the invention are organotin compounds of the general formula $(R^{11})_{4-x}$—$Sn(Y)_x$, in which Y represents a radical $OCOR^{12}$, OH or OR, wherein $R^{12}$ represents $C_1$-$C_{12}$-alkyl, $C_6$-$C_{12}$-aryl or $C_7$-$C_{13}$-alkylaryl, $R^{11}$ independently of $R^{12}$ has the meaning of $R^{12}$ and x represents an integer from 1 to 3, dialkyltin compounds having from 1 to 12 carbon atoms in the alkyl radical, or bis-(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipinate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctylate, octyltin triisooctylate, butylstannonic acid and octylstannonic acid in amounts of from 0.001 to 20 wt. % (see EP 879, EP 880, EP 39 452, DE-OS 34 45 555, JP 79/63023), polymeric tin compounds of the formula —[—RR$^{11}$Sn—O—]—, in which R and R$^{11}$ independently of one another have the meaning given above for R$^{12}$, for example poly[oxy(dibutylstannylene)], poly[oxy(dioctylstannylene)], poly[oxy(butylphenylstannylene)] and poly[oxy(diphenylstannylene)] (DE-OS 34 45 552), polymeric hydroxystannoxanes of the formula —[—RSn(OH)—O—]—, for example poly(ethylhydroxystannoxane), poly(butylhydroxystannoxane), poly(octylhydroxysnoxane), poly(undecylhydroxystannoxane) and poly(dodecylhydroxystannoxanes) in amounts of from 0.001 to 20 wt. %, preferably from 0.005 to 5 wt. %, based on dialkyl carbonate (DE-OS 40 06 420). Further tin compounds which can be used according to the invention are Sn(II) oxides of the general formula

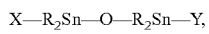

wherein X and Y independently of one another represent OH, SCN, OR$^{13}$, OCOR$^{13}$ or halogen and R represents alkyl, aryl, wherein R$^{13}$ has the meaning given above for R$^{12}$ (EP 0 338 760).

Further catalysts which can be used according to the invention are lead compounds, optionally together with triorganophosphanes, a chelate compound or an alkali metal halide, for example Pb(OH)$_2$-2PbCO$_3$, Pb(OCO—CH$_3$)$_2$, Pb(OCO—CH$_3$)$_2$.2LiCl, Pb(OCO—CH$_3$)$_3$.2PPh$_3$ in amounts of from 0.001 to 1, preferably from 0.005 to 0.25 mol per mol of dialkyl carbonate (JP 57/176932, JP 01/093580), as well as other lead(II) and lead(IV) compounds, such as PbO, PbO$_2$, red lead, plumbites and plumbates (JP 01/093560), iron(III) acetate (JP 61/1 72 852), also copper salts and/or metal complexes, for example of alkali, zinc, titanium and iron (JP 89/005588).

It is further possible to use heterogeneous catalyst systems in the process according to the invention. Such systems are, for example, mixed oxides of silicon and titanium which are obtainable by common hydrolysis of silicon and titanium halides (JP 54/125617) or titanium dioxides having a high BET surface area >20 m$^2$/g (DE-OS 40 36 594).

Preferred catalysts for the process according to the invention are the above-mentioned metal compounds AlX$_3$, TiX$_3$, UX$_4$, TiX$_4$, VOX$_3$, VX$_5$, ZnX$_2$, FeX$_3$, PbX$_2$ and SnX$_4$. Particular preference is given to AlX$_3$, TiX$_4$, PbX$_2$ and SnX$_4$, of which titanium tetrachloride, titanium tetramethoxide, titanium tetraphenoxide, titanium tetraethoxide, titanium tetraisopropylate, titanium tetradodecylate, tin tetraisooctylate and aluminium triisopropylate may be mentioned by way of example. Metal compounds TiX$_4$ are very particularly preferred. Particular preference is given to titanium tetramethoxide, titanium tetraphenoxide and titanium tetraethoxide.

The catalyst is preferably introduced into the transesterification column in dissolved or suspended form together with the stream containing the aromatic hydroxy compound(s). Alternatively, the catalyst can also be metered in separately, for example in the reaction alcohol or a suitable inert solvent. When heterogeneous catalysts are used, these can be used in admixture with the mentioned filling materials, in a suitable form instead of filling materials or as a bulk filling on any column plates fitted.

The energy required for the reaction in the transesterification column can on the one hand be produced via internal or external devices, such as, for example, heat exchangers, evaporators and/or heatable column plates, and/or on the other hand can be introduced either with the liquid stream containing the aromatic hydroxy compound(s) or with the dialkyl-carbonate-containing stream metered in gaseous form. A supply of heat can take place in this manner in particular in the region of the reaction zone(s). This heat in the region of the reaction zone(s) is preferably supplied wholly or partially by means of evaporators or heatable column plates. It is particularly advantageous to introduce the energy required for the reaction in the transesterification column into the transesterification column at least partially both with the liquid stream containing the aromatic hydroxy compound(s) and with the dialkyl-carbonate-containing stream metered in gaseous form and additionally by means of internal and/or external heat exchangers.

According to the invention, the heat of condensation obtained by condensation in the intermediate condenser(s) is fed directly or indirectly back into the process again. Within the scope of the invention, the direct feeding back of the heat of condensation into the process is to be understood as meaning that the heat of condensation is fed back into the process without an intermediate heating medium, for example for heating either a stream fed to the transesterification column or an optional second column or for heating one or more column sections. This can take place, for example, in a heat exchanger. Preferably, such a heat exchanger is combined with the intermediate condenser. Within the scope of the invention, the indirect feeding of the heat of condensation back into the process is to be understood as meaning that a heating medium is first produced with the resulting heat of condensation, which heating medium is used to feed the heat of condensation back into the process. With this heating medium it is possible, for example, to heat a stream fed to the transesterification column or to an optional second column or to heat one or more column sections. Suitable heating media are gases, vapours or liquids, preferably vaporous or liquid technical heat exchange media such as, for example, water, heat carriers based on mineral oil, or synthetic heat carriers (e.g. Diphyl™, Marlotherm®). Particularly preferred heating media are water or water vapour. In a particularly preferred embodiment of the process according to the invention, all or part of the heat of condensation obtained in the intermediate condenser is used directly or indirectly for evaporating the dialkyl carbonate introduced into the transesterification column.

The process according to the invention can be carried out continuously or discontinuously. A continuous procedure is preferred.

By the use of one or more intermediate condenser(s) in the transesterification in the transesterification column, the heat of condensation obtained in the condensation can be conveyed away at a markedly higher temperature level and can therefore be used more efficiently. As a result, the heating and cooling capacity can be reduced to an equal degree. A substantial advantage of the process according to the invention as compared with the processes of the prior art is, therefore, the marked reduction in energy consumption in the preparation of diaryl carbonates or alkylaryl carbonates. At the same time, the process can be carried out with a simple apparatus because, owing to the use of column arrangements, a complicated reactor arrangement with a plurality of separate reaction zones connected in series is not required.

Part of the process according to the invention is explained by way of example by means of FIG. 1 to 3. FIG. 1 to 3 show the process according to the invention without any subsequent steps such as disproportionation, further transesterification or purification in any further columns. An embodiment of the feeding back of the resulting heat of condensation is shown only in FIG. 2.

The figures serve to explain the invention by way of example and are not to be regarded as limiting.

In FIG. 1 to 3, the abbreviations have the following meanings:

K1 transesterification column
K2 column with separate concentrating part
C1 condenser
$C_2$ intermediate condenser
$VT_1$ lower concentrating part
$VT_2$ upper concentrating part
RZ reaction zone
AT stripping part
$E_1$ evaporator for sump product
$E_2$-$E_N$ intermediate evaporators in the reaction zone.

The following material streams are also mentioned in FIG. 1 to 3:

1 stream containing dialkyl carbonate(s) (liquid)
2 stream containing aromatic hydroxy compound(s)
3 residual vapour mixture after condensation in condenser C1
4 distillate of the transesterification column after condensation in condenser C1
5 sump product of the transesterification column after concentration by sump evaporator $E_1$
6 stream with aromatic hydroxy compounds after heating
7 stream with dialkyl carbonate after evaporation (and optional superheating)
8 vaporous mixture downstream of intermediate condenser $C_2$
9 vaporous mixture to intermediate condenser $C_2$
10 liquid leaving the upper concentrating part $VT_2$
11 condensate of the intermediate condenser $C_2$
12 vaporous mixture to condenser C1
12a liquid to the lower concentrating part $VT_1$
13 return to the upper concentrating part $VT_2$
14 flow of liquid mixture from stripping part AT
15 vapour/liquid mixture at the outlet of the evaporator $E_1$ FIG. 1 shows a transesterification column K1 into which the two starting material streams, that is to say a stream 2 containing the aromatic hydroxy compound and a stream 1 containing the dialkyl carbonate, are guided countercurrently within a countercurrent esterification in the region of a reaction zone RZ and are reacted to form alkylaryl carbonates and small amounts of diaryl carbonates.

In the case of continuous processes in particular, the stream 1 containing the dialkyl carbonate can also contain, in addition to the dialkyl carbonate, portions of the aromatic hydroxy compound, the aliphatic hydroxy compound $R^1$—OH and/or $R^2$—OH obtained in the reaction (reaction alcohol), very small amounts of the alkylaryl carbonate and/or diaryl carbonate obtained in the transesterification, and undesirable secondary components formed in the reaction. The stream 1 containing the dialkyl carbonate can contain, for example, from 0 to 5 wt. %, preferably from 0.05 to 3 wt. % and particularly preferably from 0.05 to 2 wt. %, of the reaction alcohol, from 0 to 40 wt. %, preferably from 0 to 10 wt. %, particularly preferably from 0 to 5 wt. %, of the aromatic hydroxy compound, from 0 to 5 wt. % alkylaryl carbonate, from 0 to 5 wt. % diaryl carbonate and from 0 to 5 wt. % other secondary compounds formed in the reaction (e.g. alkylaryl ethers) or impurities already contained in the starting materials, in each case based on the total weight of the dialkyl-carbonate-containing stream. The stream 1 containing the dialkyl carbonate preferably contains from 50 to 100 wt. % dialkyl carbonate, based on the total weight of the dialkyl-carbonate-containing stream, the sum of the individual components mentioned above being 100 wt. %. In continuous processes in particular, the stream 2 containing the aromatic hydroxy compound can also contain, in addition to the aromatic hydroxy compound, portions of the dialkyl carbonate, the alkylaryl carbonate and/or diaryl carbonate formed in the transesterification, very small amounts of the reaction alcohol and undesirable secondary products obtained in the reaction. For example, the content of the dialkyl carbonate can be from 0 to 50 wt. %, the content of the reaction alcohol from 0 to 10 wt. %, preferably from 0 to 5 wt. %, the content of the alkylaryl carbonate and of the diaryl carbonate in each case from 0 to 10 wt. %, preferably from 0 to 5 wt. %, and the content of undesirable secondary products from 0 to 5 wt. %, preferably from 0 to 1 wt. %, in each case based on the total weight of the stream containing the aromatic hydroxy compound. The catalyst can additionally be fed into the transesterification column with the stream 2 containing the aromatic hydroxy compound. In that case, the content of catalyst is preferably from 0 to 5 wt. %, based on the total weight of the stream containing the aromatic hydroxy compound. Preferably, the stream 2 containing the aromatic hydroxy compound contains from 50 to 100 wt. % aromatic hydroxy compound, based on the total weight of the stream containing the aromatic hydroxy compound, the sum of the amounts of the individual components mentioned above being 100 wt. %.

Before it is introduced into the column K1, the stream 1 containing the dialkyl carbonate is evaporated and optionally superheated. The stream 2 containing the aromatic hydroxy compound is heated before it is introduced into the column K1. The starting material streams 7 and 8, after evaporation and optional superheating and after heating, respectively, are guided countercurrently to one another in the reaction zone RZ, that is to say the stream 7 containing the aromatic hydroxy compound is fed in at the top end of the reaction zone RZ in heated, liquid form, and the stream 8 containing the dialkyl carbonate is fed in, in gaseous or optionally slightly superheated form, at the bottom end of the reaction zone. The aliphatic hydroxy compound $R^1$—OH and/or $R^2$—OH obtained in the reaction is drawn off in vapour form (13) at the head of the column, together with unreacted dialkyl carbonate, and the less readily volatile alkylaryl carbonate is removed at the foot of the column K1 (5) in the form of a liquid stream together with unreacted amounts of the aromatic hydroxy compound, diaryl carbonate and optionally further not readily volatile compounds. The energy required to establish the desired temperature profile can be effected inter alia at the sump of the column by one or more evaporators $E_1$. To that end, the liquid mixture (15) flowing from the stripping part, or, if a stripping part is not present, from the reaction zone, is partially evaporated. Depending on the construction of the evaporator, only vapour or a vapour-liquid mixture (stream 16) is obtained at the outlet of the evaporator. The vapour contained in the stream 16 is fed to the stripping part (AT) from beneath or, if a stripping part is not present, is fed to the reaction zone from beneath. Heat can be supplied in the region of the reaction zone by additional intermediate evaporators $E_2$-$E_N$. In the stripping part AT provided between the reaction zone RZ and the evaporator $E_1$, concentration of the resulting alkylaryl carbonate and of the diaryl carbonate takes place, the disproportionation reaction of alkylaryl carbonate to diaryl carbonate already beginning to an enhanced degree in this portion of the column K1 owing to the depletion of dialkyl carbonate.

Concentration of the aliphatic hydroxy compound formed in the reaction and of the excess dialkyl carbonate takes place in a concentrating part located between the condenser C1 and the reaction zone RZ. During this concentration, a content of aromatic hydroxy compound(s) in the distillate 4 of from 0 to 40 wt. %, preferably from 0 to 10 wt. %, particularly preferably from 0 to 5 wt. %, based on the total weight of the distillate 4, is be established. The concentrating part is divided into at least two sections, the upper and the lower concentrating parts, an intermediate condenser $C_2$ being located between the upper concentrating part $VT_2$ and the lower concentrating part $VT_1$. The intermediate condenser $C_2$ condenses a portion of the vapours 10 rising from the lower concentrating part $VT_1$. The vaporous mixture 10 entering the intermediate condenser $C_2$ preferably contains from 10 to 70 wt. % aromatic hydroxy compound. The condensation temperature in the intermediate condenser $C_2$ is therefore markedly higher as compared with the condensation temperature in the head condenser C1, owing to the comparatively larger amounts of aromatic hydroxy compound. Depending on the operating pressure and the position of the concentration profile, the condensation temperature in the intermediate condenser can preferably be in the range from 100 to 300° C., particularly preferably from 120 to 250° C., most particularly preferably from 150 to 240° C., and in the head condenser preferably in the range from 0 to 250° C., particularly preferably from 40 to 200° C. The condensate 12 formed in the intermediate condenser $C_2$ and the liquid 11 flowing from the upper concentrating part $VT_2$ located above it are guided onto the lower concentrating part $VT_1$. The vaporous mixture downstream of the intermediate condenser passes into the upper concentrating part $VT_2$. The vapour 13 coming from the upper concentrating part $VT_2$ is condensed to the greatest possible extent in the condenser C1, part of the condensate being fed back to the upper concentrating part $VT_2$ again as reflux (14) and part being removed as distillate stream 4. The distillate stream 4 contains substantially the dialkyl carbonate used in excess and the corresponding aliphatic hydroxy compound $R^1$—OH and/or $R^2$—OH formed in the reaction, and optionally small amounts of the aromatic hydroxy compound. The residual vapour mixture from the condenser C1 is removed as vapour stream 3.

The heat of condensation liberated in the intermediate condenser $C_2$ can be fed directly or indirectly back into the process again as described above for the process according to the invention (not shown in FIG. 1).

FIG. 2 shows a particularly preferred embodiment of the process according to the invention, in which the intermediate condenser is constructed separately outside the column and the heat of condensation obtained in the condensation of the stream 10 in the intermediate condenser $C_2$ is used for the evaporation of the dialkyl-carbonate-containing stream 1 used in the countercurrent esterification in the esterification column K1. To that end, the dialkyl-carbonate-containing stream 1 is fed to an evaporation unit $C_2$, is evaporated wholly or partially and is optionally also superheated. The vaporous mixture 10 of the lower concentrating part $VT_1$ is fed to the intermediate condenser $C_2$, where it partially condenses. The condensate 12 formed thereby is fed to the lower concentrating part $VT_1$ again, the uncondensed vapours are fed into the upper concentrating part $VT_2$. Otherwise, the process shown in FIG. 2 corresponds to that shown in FIG. 1. The explanations given above for FIG. 1 therefore apply analogously.

FIG. 3 shows a further particularly preferred embodiment of the process according to the invention, in which the intermediate condenser $C_2$ and the upper concentrating part $VT_2$ are not integrated in the transesterification column K1 but are constructed separately outside the column K1. The vaporous mixture 10 leaving the lower concentrating part $VT_1$ is thereby fed to the intermediate condenser $C_2$, where it partially condenses. The residual vapour is fed to the upper concentrating part $VT_2$, which is accommodated in a separate column K2. The liquid 11 coming from the upper concentrating part $VT_2$ is fed together with the condensate 12 from the intermediate condenser $C_2$ to the lower concentrating part (12a). The vapour 13 coining from the upper concentrating part $VT_2$ is condensed to the greatest possible extent, part of the condensate being fed back to the upper concentrating part $VT_2$ again as reflux (14) and part being removed as distillate stream 4. The distillate stream 4 contains substantially the dialkyl carbonate used in excess and the corresponding aliphatic hydroxy compound $R^1$—OH and/or $R^2$—OH formed in the reaction, and optionally small amounts of the aromatic hydroxy compound. The residual vapour mixture from the condenser C1 is removed as vapour stream 3. Otherwise, the process shown in FIG. 3 corresponds to that shown in FIG. 1. The explanations given above for FIG. 1 therefore apply analogously.

Suitable transesterification columns for the process according to the invention containing at least one intermediate condenser have not hitherto been described in the literature. Therefore, the present invention further provides a column for the reaction of dialkyl carbonates with aromatic hydroxy compounds in the presence of at least one transesterification catalyst for the preparation of diaryl carbonates and/or alkylaryl carbonates, comprising
   at least one inlet for the dialkyl carbonate(s) and at least one inlet for the aromatic hydroxy compound(s),
   at least one outlet for the gaseous head product in the upper portion of the column and at least one outlet for the liquid sump product in the lower portion of the column,
   at least one concentrating part in the upper portion of the column and at least one reaction zone beneath a concentrating part, which has at least two sections,
   wherein at least one concentrating part is equipped with at least one intermediate condenser.

Preferably, the transesterification column according to the invention has in the region of the reaction zone a diameter $D_{RZ}$ of from 400 to 20,000 mm and the reaction zone has a length $L_{RZ}$ of from 5000 to 60,000 mm. Also preferably, the transesterification column according to the invention has in the reaction zone a number of theoretical stages $n_{RZ}$ of from 5 to 50.

The reaction zone can additionally have a number of intermediate heaters $n_E$. The ratio of the number of intermediate heaters $n_E$ in the reaction zone to the number of theoretical stages $n_{RZ}$ is preferably from 0 to 2.

Also preferably, the transesterification column according to the invention has in the region of the stripping part which is optionally present a diameter $D_{AT}$ of from 100 to 20,000 mm and the stripping part has a length $L_{AT}$ of from 100 to 20,000 mm. Also preferably, the transesterification column according to the invention has in the stripping part a number of theoretical stages $n_{AT}$ of from 0 to 20.

Preferably, the concentrating part of the transesterification column according to the invention has a diameter $D_{VT}$ of from 200 to 10,000 mm and the entire region of the concentrating part—including the upper and lower concentrating parts and the intermediate condenser which may be present—has a length $L_{VT}$ of from 100 to 30,000 mm, preferably from 500 to 30,000 mm. Also preferably, the concentrating part has a total number of theoretical stages $n_{VT}$ of from 2 to 20.

In preferred embodiments, the lower concentrating part of the transesterification column according to the invention has a diameter $D_{VT1}$ of from 200 to 10,000 mm and a length $L_{VT1}$ of from 200 to 10,000 mm, and the upper concentrating part of the transesterification column according to the invention has a diameter $D_{VT2}$ of from 200 to 10,000 mm and a length $L_{VT2}$ of from 200 to 10,000 mm. The ratio of the diameter of the lower concentrating part to the column diameter in the reaction zone $D_{VT1}:D_{RZ}$ is preferably from 0.3 to 1, and the ratio of the diameter of the upper concentrating part to the column diameter in the reaction zone $D_{VT2}:D_{RZ}$ is preferably from 0.1 to 1.

In further preferred embodiments, the intermediate condenser of the transesterification column according to the invention has a length $L_{C2}$ of from 100 to 10,000 mm and the ratio of the diameter of the intermediate condenser to the column diameter in the reaction zone $D_{C2}:D_{RZ}$ is preferably from 0.1 to 1. Also preferably, the intermediate condenser has a heat transfer area $A_{C2}$ of from 1 to 5000 m².

The intermediate condenser can be integrated in the column or can be in the form of a separate intermediate condenser outside the transesterification column. Furthermore, it is also possible for the intermediate condenser and the upper section of the concentrating part not to be integrated in the transesterification column but to be accommodated separately outside the transesterification column. Various constructions are possible according to the invention for the intermediate condenser, such as, for example, a plate-type heat exchanger or tubular heat exchanger. Such constructions are known to the person skilled in the art.

The dimensions and characteristic data of the transesterification column according to the invention given above preferably apply for a product amount of more than 100 kg/h, product amounts optionally being understood as meaning the sum of the alkylaryl carbonate and/or diaryl carbonate contained in the sump product. The person skilled in the art knows how to convert the given dimensions to smaller product amounts. The present invention also provides transesterification columns resulting from such conversions.

The preferred ranges indicated above for the first transesterification column in the process according to the invention also apply to the column according to the invention.

Examples of particularly preferred embodiments of the column according to the invention are to be found in FIG. 1 to 3.

The examples which follow serve to illustrate the invention by way of example and are not to be regarded as limiting.

EXAMPLES

Example 1

According to the Invention

In a transesterification column comprising
an upper concentrating part (VT$_2$) having 4 theoretical stages,
an intermediate condenser (C$_2$),
a lower concentrating part (VT$_1$) having 4 theoretical stages,
a reaction zone (RZ) having 30 reaction plates (hold-up: 12 l), 3 plates being equipped with heating elements, and
a stripping part AT having 6 plates (hold-up: 12 l),
400 kg/h of a mixture of 85.4 wt. % phenol, 9.2 wt. % dimethyl carbonate, 3.2 wt. % diphenyl carbonate, 1.5 wt. % titanium tetraphenolate, 0.3 wt. % anisole, 0.3 wt. % methylphenyl carbonate and 0.1 wt. % methanol are metered in at the top end of the reaction zone. At the bottom end of the reaction zone, 539.6 kg/h of a vapour mixture, superheated by 5° C., of 98.8 wt. % dimethyl carbonate, 0.9 wt. % phenol, 0.2 wt. % anisole and 0.1 wt. % methanol are fed in.

456.9 kg/h of a product mixture consisting of 51 wt. % phenol, 27.3 wt. % MPC (124.7 kg/h), 11.9 wt. % DPC (54.3 kg/h), 8.1 wt. % DMC, 0.4 wt. % anisole and 1.3 wt. % titanium tetraphenolate are obtained at the sump of the column.

The transesterification column is operated at a head pressure (above VT$_2$) of 3.6 bar and a reflux ratio of 1.15. A temperature of 230° C. is established in the sump of the column, and a mean reaction temperature of 215° C. is established in the reaction zone. A sump evaporator E$_1$ and intermediate evaporators E$_2$-E$_4$ in the reaction zone are operated with hot vapour at a vapour pressure of 35 bar, a natural recirculating evaporator being used as the sump evaporator E$_1$ and damping registers integrated in the reaction plates being used as intermediate evaporators. The inlet temperature into the intermediate condenser is 205° C., the outlet temperature is 193° C. and the cooling capacity is 57 kW. The heat of condensation formed in the intermediate condensation can be used to produce hot vapour having a hot vapour pressure of 8 bar (dewpoint: 170.4° C.). The heating capacity required for evaporation of the dimethyl-carbonate-containing stream is 52 kW. The evaporation and superheating of the dimethyl carbonate are carried out at a temperature of from 135 to 152° C., for which purpose the vapour used in the intermediate condenser can be used without difficulty.

Without the use of the intermediate condenser C$_2$ and the use of the waste heat produced thereby, the energy consumption of the transesterification, including the heating capacity of the evaporators E$_1$ and E$_2$-E$_N$ and that required for the evaporation of the dimethyl-carbonate-containing stream, would be 183 kW. By using the intermediate condenser it is possible to make a saving in terms of heating capacity of 52 kW, that is to say 28%. If it is additionally taken into account that 57 kW of heat are conveyed away in the intermediate condenser, an excess of vapour (5 kW) is additionally produced, which can optionally be used in other ways. The heat of condensation at the head condenser (C1) is 126 kW and takes place in the temperature range 137-115° C. Without the use of the intermediate condenser, this would be approximately 183 kW. The cooling capacity is accordingly reduced markedly, that is to say by 31%, by using the intermediate condenser.

Example 2

According to the Invention

In a column comprising
an upper concentrating part (VT$_2$) having 6 theoretical stages,
an intermediate condenser (C$_2$),
a lower concentrating part (VT$_1$) having 6 theoretical stages,
a reaction zone (RZ) having 35 reaction plates (hold-up: 12 l), without an intermediate evaporator, and
a stripping part (AT) having 9 plates (hold-up: 12 l),
473.2 kg/h of a mixture of 94.46 wt. % phenol, 1.41 wt. % dimethyl carbonate, 2.75 wt. % diphenyl carbonate, 1.3 wt. % titanium tetraphenolate, 0.01 wt. % anisole, 0.02 wt. % methylphenyl carbonate and 0.05 wt. % methanol are metered in at the top end of the reaction zone. At the bottom end of the reaction zone, 477.4 kg/h of a vapour mixture, superheated by 20° C., consisting of 98.3 wt. % dimethyl carbonate, 1.5 wt. % phenol, 0.1 wt. % anisole and 0.1 wt. % methanol are fed in.

489.2 kg/h of a product mixture consisting of 69.18 wt. % phenol, 6.32 wt. % MPC (30.9 kg/h), 23.03 wt. % DPC (112.7 kg/h), 0.2 wt. % DMC, 0.01 wt. % anisole and 1.26 wt. % titanium tetraphenolate are obtained at the sump of the column.

The transesterification column is operated at a head pressure (above VT$_2$) of 2 bar and a reflux ratio of 1.15. The phenol content in the distillate was 2 wt. %. A temperature of 227° C. is established in the sump of the column, and a mean reaction temperature of 200° C. is established in the reaction zone. A sump evaporator $E_1$ is operated with hot vapour at a vapour pressure of 35 bar, a natural recirculating evaporator being used as the sump evaporator $E_1$.

The inlet temperature into the intermediate condenser is 190° C., the outlet temperature is 183° C. and the cooling capacity is 46 kW. The heat of condensation formed in the intermediate condensation can be used to produce hot vapour having a hot vapour pressure of 8 bar (dewpoint: 170.4° C.). The evaporation and superheating of the dimethyl carbonate are carried out at a temperature of from 122 to 153° C., for which purpose the vapour used in the intermediate condenser can be used without difficulty. The heating capacity required for evaporation of the dimethyl-carbonate-containing stream is 46 kW.

Without the use of the intermediate condenser $C_2$ and the use of the waste heat produced thereby, the energy consumption of the transesterification, including the heating capacity of the evaporators $E_1$ and $E_2$-$E_N$ and that required for the evaporation of the dimethyl-carbonate-containing stream, would be 190 kW. By using the intermediate condenser it is possible to make a saving in terms of heating capacity of 46 kW, that is to say 24%. The heat of condensation at the head condenser (C1) is 144 kW and takes place in the temperature range 137-115° C. Without the use of the intermediate condenser, this would be 190 kW (see Comparison Example 3). The cooling capacity is accordingly reduced markedly, that is to say by 24%, by using the intermediate condenser.

Comparison Example 3

Under otherwise identical conditions to those in Example 2, the transesterification column was operated without an intermediate condenser. In order to achieve a phenol content of 2 wt. % in the distillate, the reflux ratio had to be raised to 2.

The cooling capacity of the head condenser C1 was 190 kW, that of the evaporator was 144 kW. The condensation in the head condenser C1 took place at temperatures from 125 to 97° C.

Owing to the comparatively low temperature level in the condensation in the head condenser, the resulting heat of condensation is no longer usable for many processes and must therefore ultimately be dissipated by means of cooling water or air cooling.

According to the invention, therefore, by means of a construction with an intermediate condenser, energy is removed from the stream of material in the column at a higher temperature level than at the head condenser, so that the energy can be used for the evaporation of a stream fed to the column. A saving of considerable amounts of energy is associated therewith.

All the references described above are incorporated by reference in its entirety for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

We claim:

1. A process for the preparation of a mixture of at least one diaryl carbonate and at least one alkylaryl carbonate or a mixture thereof from at least one dialkyl carbonate and at least one aromatic hydroxy compound, which comprises (a) reacting the dialkyl carbonate(s) in the presence of at least one transesterification catalyst with the aromatic hydroxy compound(s) in at least one transesterification column containing at least one concentrating part in the upper portion of the column and at least one reaction zone beneath the concentrating part, which has at least two sections, (b) removing the vapor at the head of the transesterification column is condensed wholly or partially in at least one condenser, equipping at least one concentrating part of the transesterification column with at least one intermediate condenser, and the heat of condensation obtained by condensation in that intermediate condenser is fed directly or indirectly back into the process again;

wherein the at least one diaryl carbonate is of the formula (I)

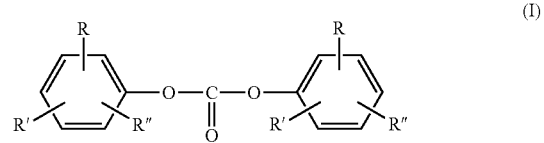

wherein R, R' and R" independently of one another represent H, linear or branched, optionally substituted $C_1$-$C_{34}$-alkyl, $C_1$-$C_{34}$-alkoxy, $C_5$-$C_{34}$-cycloalkyl, $C_7$-$C_{34}$-alkylaryl, $C_6$-$C_{34}$-aryl or a halogen radical, and R, R' and R" on both sides of formula (I) can be the same or different, R can further represent —COO—R''', wherein R''' can be H, optionally branched $C_1$-$C_{34}$-alkyl, $C_1$-$C_{34}$-alkoxy, $C_5$-$C_{34}$-cycloalkyl, $C_7$-$C_{34}$-alkylaryl or $C_6$-$C_{34}$-aryl; and wherein the at least one alkylaryl carbonate is of the general formula (IV)

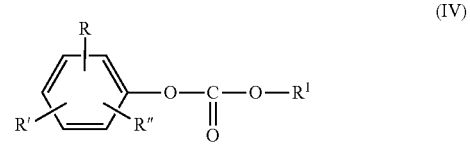

wherein $R^1$ represents a linear or branched, optionally substituted $C_1$-$C_{34}$-alkyl.

2. The process according to claim 1, wherein the transesterification column has at least one stripping part beneath a reaction zone.

3. The process according to claim 1, wherein part of the condensate obtained in the condensation of the vapor removed at the head of the transesterification column is applied to the transesterification column again as reflux.

4. The process according to claim 1, wherein all or part of the heat of condensation that is obtained is used directly or indirectly for the evaporation of the dialkyl carbonate introduced into the transesterification column.

5. The process according to claim 1, wherein the intermediate condenser is integrated in the transesterification column or is in the form of a separate intermediate condenser outside the column.

6. The process according to claim 1, wherein the concentrating part of the transesterification column, which is equipped with at least one intermediate condenser, is divided into a lower and an upper concentrating part, of which the lower concentrating part is located beneath the intermediate condenser and the upper concentrating part is located above the intermediate condenser.

7. The process according to claim 6, wherein the intermediate condenser and the upper concentrating part are integrated in the transesterification column or are in the form of a separate device outside the column.

8. The process according to claim 1, wherein the temperature of the reaction zone is in the range from 100 to 300° C. and the pressure of the reaction zone is in the range from 0.5 to 20 bar.

9. The process according to claim 7, wherein the temperature of the reaction zone is in the range from 120 to 250° C. and the pressure of the reaction zone is in the range from 0.8 to 15 bar.

10. The process according to claim 1, wherein the temperature of the reaction zone is in the range from 150 to 240° C. and the pressure of the reaction zone is in the range from 0.9 to 10 bar.

11. The process according to claim 1, wherein R, R' and R" represent H.

12. The process according to claim 1, wherein the diaryl carbonate is diphenyl carbonate, the dialkyl carbonate is dimethyl carbonate or diethyl carbonate, and the aromatic hydroxy compound is phenol.

13. The process according to claim 1, wherein $R^1$ represents a $C_1$-$C_6$alkyl.

14. The process according to claim 13, wherein $R^1$ represents a $C_1$-$C_4$-alkyl.

* * * * *